(12) United States Patent
Byrd

(10) Patent No.: US 6,316,686 B1
(45) Date of Patent: Nov. 13, 2001

(54) MEDICAL PRESSURE DRESSING AND PROCESS

(76) Inventor: Timothy N. Byrd, 1267 Old Cades Cove Rd., Townsend, TN (US) 37882

( * ) Notice: Subject to any disclaimer, the term of this patent is extended or adjusted under 35 U.S.C. 154(b) by 0 days.

(21) Appl. No.: 09/597,047

(22) Filed: Jun. 20, 2000

(51) Int. Cl.$^7$ .................................................... A61F 13/00
(52) U.S. Cl. ............................. 602/41; 602/42; 602/43; 602/44; 602/45; 602/46; 602/47
(58) Field of Search ................................ 602/41–47, 53, 602/56, 64–66; 128/109.1, 101.1, 108.1

(56) References Cited

U.S. PATENT DOCUMENTS

| | | |
|---|---|---|
| 3,490,448 | 1/1970 | Grubb . |
| 4,221,215 * | 9/1980 | Mandelbaum ...................... 604/327 |
| 4,377,159 | 3/1983 | Hansen . |
| 5,507,721 | 4/1996 | Shippert . |
| 5,618,556 * | 4/1997 | Johns et al. ......................... 424/448 |
| 5,690,610 | 11/1997 | Ito . |
| 5,800,372 | 9/1998 | Bell . |
| 5,891,074 | 4/1999 | Cesarczyk . |

* cited by examiner

Primary Examiner—Michael A. Brown
Assistant Examiner—Lalita M. Hamilton
(74) Attorney, Agent, or Firm—Susan F. Johnston

(57) ABSTRACT

The invention disclosed herein is a medical pressure dressing. The dressing includes a frame for affixing to skin surrounding the skin treatment site and a strap for covering the frame and wound. The frame has a channel extending therethrough providing an orifice over the skin treatment site. The strap includes, or else includes means for attachment to, a plunger that is shaped for being received downwardly through the channel and against the wound when the strap is extended across the frame.

The present application further discloses a process for treating a wound that includes a tissue covered by a skin treatment site. The process includes reducing the elasticity of the skin treatment site by affixing a frame having an elasticity less than the elasticity of the skin treatment site around the skin treatment site, and performing an elasticity-sensitive procedure on the wound. Examples of elasticity-sensitive procedures include pushing, cutting, puncturing, rubbing, and such.

20 Claims, 3 Drawing Sheets

MEDICAL PRESSURE DRESSING AND PROCESS

FIELD OF THE INVENTION

The present invention relates to medical dressings. The present invention more particularly relates to medical pressure dressings used to effect hemostasis of a wound.

BACKGROUND OF THE INVENTION

Traditionally, in order to stop bleeding wounds, for example when an artery is bleeding, healthcare workers have applied digital pressure to the wound by manually pressing against the wound. Unless the patient is able to provide the digital pressure himself, this manual digital pressure procedure for controlling bleeding if often time-consuming for a healthcare provider administering the procedure, thus significantly adding to the medical treatment costs.

Attempts have been made to provide pressure dressings that simulate the application of digital pressure exerted from a healthcare provider or the patient. U.S. Pat. No. 3,490,448 (Grubb) discloses an adhesive pressure bandage generally consisting of a pad attached to the center of a single-sided strip of tape. That design has been found to provide very limited pressure to a puncture site due to the fact that the two opposing ends of tape adhered to a patient's skin tend to be drawn toward each other, thus reducing the downward pressure exerted by the pad. U.S. Pat. No. 5,690,610 (Ito et al.) discloses a similar pressure bandage wherein the adhesive strip covering the pressure pad is formed from a stretchable material having a high recovery property. This high recovery property promotes shrinking of the material after being extended to cover the wound. Ito et al. teach that the shrinking action of the base material atop of the pressure pad causes the pressure pad to be pressed downward as the base and the skin surrounding the pressure pad are pulled toward the pad. This device is disruptive to the skin surrounding the wound. U.S. Pat. No. 5,891,074 (Cesarczyk) discloses a pressure bandage incorporating a compressed spring held against a wound by a cover adhered to the skin. Cesarczyk teaches using a folded sheet of fold-resistant material to exert pressure to exert a downward force against the wound site as it attempts to open to an unfold state. The drawback of this springing pressure device is that the springing action of the folded sheet is exerted in both an upward and downward direction. Thus, the spring exerts a force upwardly against the cover, pulling the skin inwardly toward the wound, and thus reducing the effectiveness of the downward pressure.

It would be desirable to provide a pressure dressing adapted so that a greater amount of the force exerted by the pressure pad is directed downwardly toward the wound. It would further be desirable if such pressure dressing caused minimum pulling of the skin surrounding the wound.

SUMMARY OF THE INVENTION

The present invention includes a medical dressing for framing and covering a wound, wherein the wound has a hardness and includes a tissue covered by skin, wherein said skin includes an affixable skin annulus surrounding a skin treatment site having a first elasticity. The present medical dressing comprises:
  (a) a strap having an upper strap surface and a lower strap surface, wherein said lower strap surface includes a center area between a first plurality of opposingly positioned attachment sites; and
  (b) a frame having a second elasticity less than the first elasticity of the skin, wherein said frame has a lower frame surface positionable against the skin and an upper frame surface positionable against said lower strap surface with said upper frame surface having a second plurality of attachment sites corresponding to the positionment of said first plurality of attachment sites of said strap, said frame defining a channel extending transversely through said upper and lower frame surfaces and having a channel length, wherein said frame radiates outwardly from said channel and extends to an outermost frame edge;
  (c) a means for affixing said first plurality of attachment sites to said second plurality of attachment sites;
  (d) a means for affixing said lower frame surface to a sufficient amount of the skin annulus to reduce the elasticity of the skin treatment site; and
  (e) a means for affixing a plunger of a sufficient size for being received through said channel against the center area of said strap so that the plunger is received through said channel when said upper frame surface is positioned against said lower strap surface.

DETAILED DESCRIPTION

Figure 1:
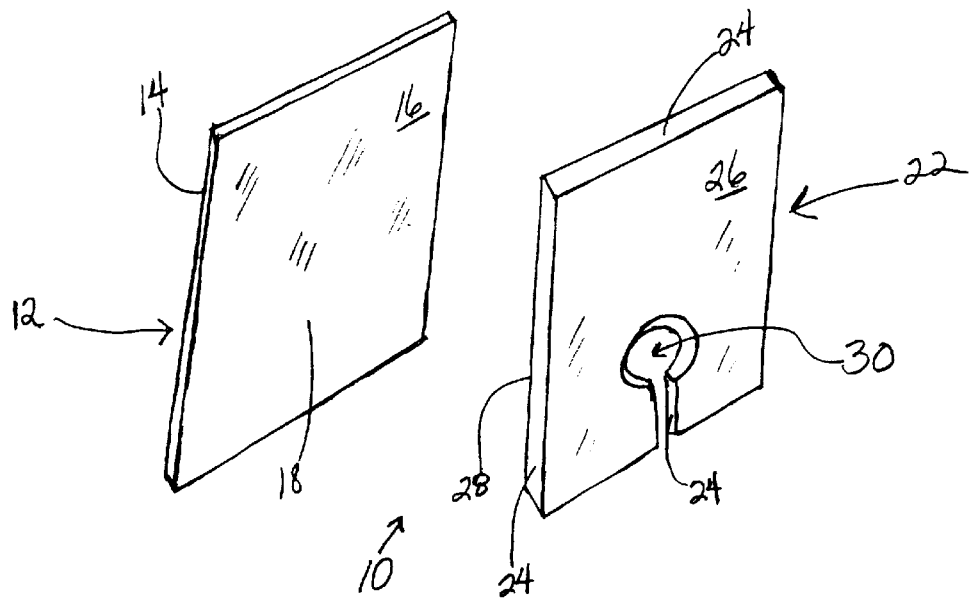
FIG. 1 illustrates a perspective view of a two-component embodiment of the dressing of the present invention wherein the strap and frame are not connected prior to use.

The applicant has developed a medical dressing and process for reducing the elasticity of a skin treatment site in preparation for treating a wound with most any elasticity-sensitive procedure. The wound may be any type of bleeding or non-bleeding wound. As used herein, a "wound" is a human or animal body tissue covered with skin. The tissue is preferably a soft tissue such as muscles, organs, arteries, and other non-bone tissues. Hardness, as used herein, is measured as the depth of the indentation created in an object (or wound) when pressed against another object. Accordingly, the hardness of a wound is determined from the amount of indentation created by pressing an article against the skin portion of the wound and toward the tissue. In the present invention, the skin portion of the wound includes a skin treatment site 2, and an annular area of skin that surrounds the skin treatment site and is sufficiently affixable to support adhesive or mechanical affixing of a dressing thereto. The skin annulus may have any shape conforming around the skin treatment site, not necessarily being a circular or other regular-shaped band. An "elasticity sensitive procedure" is a procedure, such as puncturing, cutting, rubbing, or applying blunt pressure, that effects stretching of the skin portion of the wound when conducted.

In the present invention, the applicant has discovered that when a sharp or blunt object is pressed against a wound during medical treatment, the object effects an increasingly more precise effect to the tissue portion of the wound as the elasticity of the skin treatment site is increasingly reduced. The present invention includes a medical dressing that, when applied to the wound, causes a beneficial reduction in the elasticity of the skin treatment site. Reducing the elasticity of the skin treatment site is referred to herein as "framing" the wound.

The medical dressing of the present invention is designed to frame the skin treatment site of a wound and press an object against the framed skin treatment site of the wound, thus providing pressure to the wound. The most preferred embodiment of the medical dressing of the present invention is shown as item 10 in FIG. 1 and includes a strap 12 having an upper strap surface 14 and a lower strap surface 16, wherein the lower strap surface 16 includes a center area 18 between a first plurality of opposingly positioned attachment sites. The medical dressing 10 further includes a frame 22 having an elasticity less than the elasticity of the skin component of the wound. The frame 22 has a lower frame surface 26 positionable on the skin 4 and an upper frame surface 28 positionable against the lower strap surface 16. The frame 22 defines a channel 30 extending transversely through the upper and lower frame surfaces. The frame 22 radiates outwardly from the channel 30 and extends to an outermost frame edge 24. The upper frame surface 28 includes a second plurality of attachment sites corresponding to the positionment of the first plurality of attachment sites on the strap 12 so that the strap may be tautly secured across the frame at the attachment sites. It should be understood that the outermost edge or perimeter of the frame and the strap may form shapes quite different from each other and be of different size, as long as the positionment of the first and second plurality of attachment sites correspond sufficiently so as to allow for attachment of the strap to the frame at the attachment sites. The present medical dressing also includes a means for affixing the first plurality of attachment sites of the strap to the second plurality of attachment sites of the upper frame surface 28 so that the center area 18 of the strap crosses the channel 30. Additionally included in the present medical dressing is a means for affixing the lower frame surface 26 to the skin annulus.

The medical dressing of the present invention is adapted to press an object against the framed skin treatment site while covering the wound. Such an object is most preferably a blunt object designed to simulate the application of digital pressure to the substrate. However, the present medical dressing may also be adapted to press a sharp object such as a needle into the wound.

Figure 2:
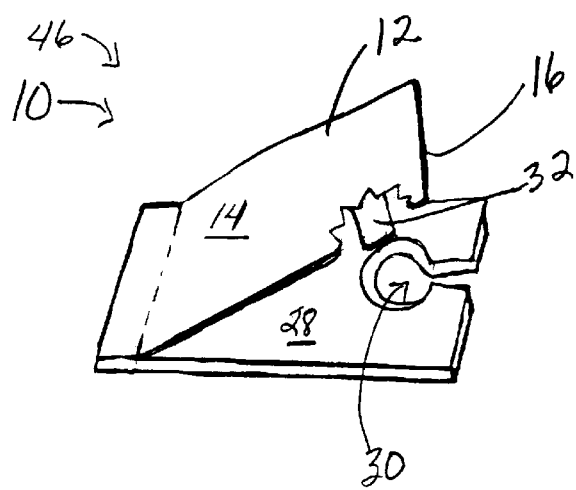
FIG. 2 illustrates a perspective view of a two-component embodiment of the present dressing wherein the strap and frame are connected at a position distal from the channel prior to use. A portion of the strap is cutaway so as to show the plunger.

The medical dressing of the present invention includes a means for affixing a blunt or sharp object against the center area 18 of the strap so that, if the object is of sufficient size, the object is slidingly received through the channel when the upper frame surface 26 is extendedly positioned against and across the lower strap surface 16. An object useful in the present dressing may have any three-dimensional shape including the box shape of traditional pressure bandage pads and gauze, but is most effective when having a bullet or plunger-type shape. Thus, the object is hereinafter referred to as a plunger 32 for descriptiveness. FIG. 2 illustrates the plunger 32 affixed to the center area 18 of the strap 12.

The medical dressing of the present invention is used by affixing a sufficient amount of the lower frame surface 26 to the annulus around the skin treatment site of a wound so that the elasticity of the treatment site is reduced. This "framing" of the skin reduces the elasticity of the treatment site by eliminating the ability of the skin surrounding the skin treatment site and wound to be stretched inwardly toward the skin treatment site. As used herein, the elasticity of the skin treatment site is considered to be reduced when less of the skin surrounding the skin treatment site (including the annulus and the skin surrounding the annulus) is pulled toward the skin treatment site when an object is pressed against the skin treatment site of the wound. For example, the amount of pulling of the skin surrounding the skin treatment site can be indicated by measuring the distance from the skin treatment site to the farthest point in each direction on the surrounding skin where movement of the skin is exhibited. A reduction in elasticity of the skin treatment site provided by the present dressing is preferably at least 25% of the initial skin elasticity prior to framing, with a reduction of at least 50% being more preferable.

The medical dressing of the present invention may be used during a pressure-sensitive procedure by framing the skin treatment site with the frame 22 prior to performing the procedure and then covering the treated wound with the strap 12 equipped with a plunger after the procedure is conducted so that pressure is applied to the treated wound. For instance, a surgeon may use the medical dressing to frame an area of skin prior to forming a fine subcutaneous incision and suture then use the pressure strap to cover the wound without further disturbing the skin surrounding the wound.

Figure 3:
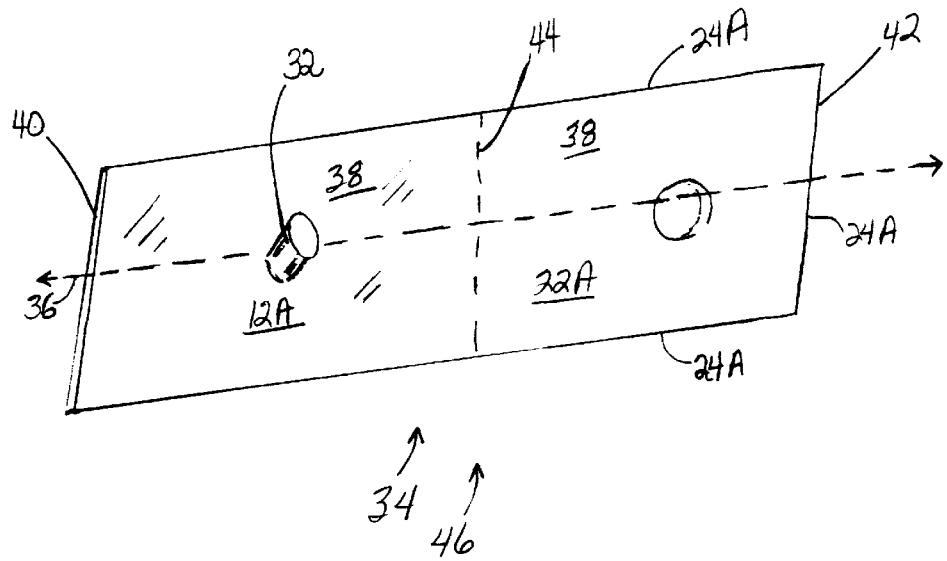
FIG. 3 illustrates a top view of the upper surface of a single-component embodiment of the dressing and pressure device of the present invention.

Another alternative embodiment of the present medical dressing is shown in FIG. 3 and is an integrally formed single-plane film 34 designed to be inwardly folded to provide the dressing of the present invention. This embodiment of the medical dressing is an elongated film 34 having an elasticity less than the elasticity of the surface of the substrate and having a longitudinal axis 36 and an upper film surface 38 and a lower film surface centered about a plane. The film has a center area positioned longitudinally between a first end 40 and a second end 42, with a transverse fold line 44 disposed across the center area. The film 34 defines a strap 12A between the first end and the fold line 44. The strap portion of the upper film surface 38 includes a center area 18A having a first diameter between a plurality of opposingly positioned attachment sites. The film 34 further defines a frame 22A between the second end 42 and the fold line 44. The frame 22A extends to an outermost frame edge 24A that extends from the fold line around the frame. The frame 22A defines a channel 30A that extends transversely from the upper surface to the lower surface and the frame radiates outwardly from the channel extending to the outermost frame edge. The fold line 44 of this single plane embodiment of the present medical dressing must be disposed so that, when the film is inwardly folded, the frame 22A and the strap 12A overlappingly correspond with each other the same as the frame corresponds with the strap in the other two-component embodiments described above.

In the design of the present medical dressing, it is of utmost importance that the first plurality of attachment sites on the strap, as well as the corresponding second plurality of attachment sites of the frame, is of sufficient number and sufficient positionment so that the center area of the strap is tautly extended across the channel of the frame when the strap is affixed to the frame at the corresponding attachment sites. This is important since, when the plunger is pressed downwardly into the wound, the wound will tend to exert a negative pressure against the strap, thus pulling the strap away from the frame. The sufficiency of the number and positionment of attachment sites will necessarily depend upon the strength of the particular means used to affix the attachment sites of the strap to the frame. It is preferred that the plurality of attachment sites essentially encircle the center area 18 of the strap, so as to extend the strap tautly in all directions.

FIG. 2 illustrates a preferred embodiment of the present medical dressing 10 especially suited to reduce the effect of a negative pressure from the plunger pushing against the strap. In this embodiment, the strap 12 is connected to a portion of the frame 22 to create a hinged relationship between the frame 22 and the strap 12 at a position distal from the channel 30. This hinged relationship is especially useful when the overlapping surfaces of the strap and frame that are semi-permanently or permanently attached to each other or integrally formed together to create the hinge accounts for at least about 15%, and more preferably at least about 25%, of the surface area where the strap overlaps the frame when the strap is extended across the dressing. A greater permanent or semi-permanent connection between the strap and frame creates a greater resistance against the strap being pulled away from the frame upon a negative pressure exerted by the plunger against the strap.

In the present medical dressing, the means for affixing a plunger to the strap, the means for affixing the attachment sites of the strap to the attachment sites of the frame, and the means for affixing the lower frame surface to the substrate may each be an adhesive or any suitable fastening mechanism. A pressure sensitive adhesive is the preferred affixing means for use in the present invention. A strip of single-sided tape provides a suitable strap equipped with an adhesive surface in the center area 18 for affixing the plunger and an adhesive area surrounding the center area (a plurality of adjacently positioned attachment sites 20) sufficient for bonding the strap to the upper frame surface 28. A releasable pressure sensitive adhesive is the most preferable means for affixing the frame to the substrate. In addition to adhesives, various fastening mechanisms are also suitable, according to the specific application. Examples of useful fastening mechanisms include any type of male-female mating members such as nuts and screws, rivets, and the like. Other types of fastening mechanisms includes buckles, straps, clamps, staples, and hook-and-loop fasteners (VELCRO®), with the hook-and-loop fasteners being a preferred type of releasable fastener for affixing the object to the strap and affixing the strap to the frame.

In the medical dressing of the present invention the frame 22 and strap 12 are preferably essentially planar components. The strap preferably has essentially the same outer shape as the frame. However, the strap can alternatively be a simple elongated cord extended across the frame so as to extend across the channel and affix to opposite sides of the frame. Any other strap shapes such as an "X" shaped strap are also suitable.

The strap is preferably made of a planar film or any of the absorbent or nonabsorbent, woven or non-woven materials commonly used to manufacture bandages. It is preferred that the strap be formed of a material having a higher hardness than the wound so as to exert more pressure downward toward the tissue portion of the wound. A strap is harder than a wound if a plunger forms a greater indentation into the wound than the strap when pressed between the strap and the wound. The strap may be formed from a material that is stretchable across the frame for affixing to the frame as long as the strap material has such a low recovery property that the material would not tend to shrink back to it's unstretched size during use. Examples of suitable strap materials include polyethylenes, polyesters, polyurethanes, and foams. Particularly useful commercially available polyesters include 3M 1526 Polyester, 3M 1506 Polyester, and 3M 9877 Polyester, available from the 3M Company.

Figure 8:
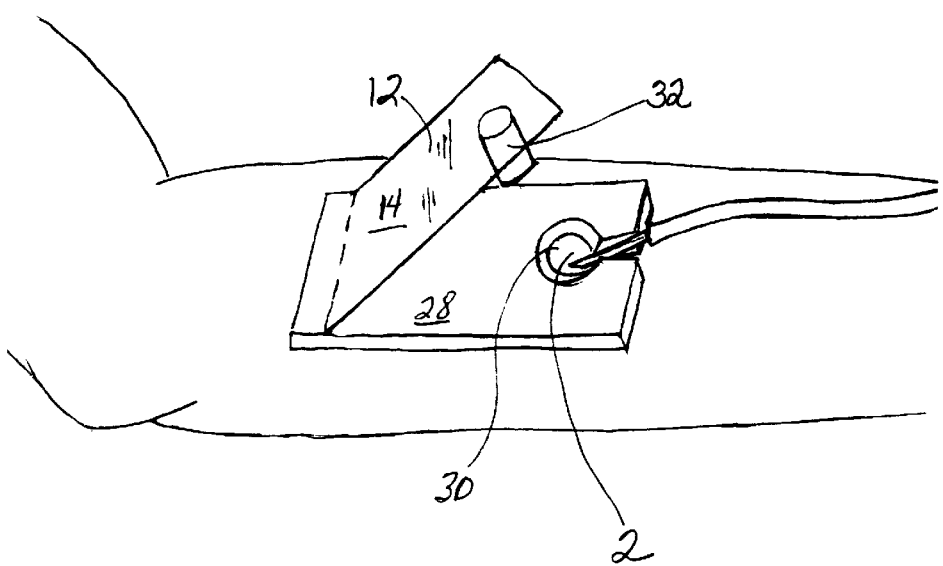
FIG. 8 illustrates the use of an embodiment of the pressure device of the present invention in conjunction with an arterial catheterization procedure.

The frame 22 must have a shape sufficient to reduce the elasticity of the skin treatment site when the frame is affixed to the affixable annular portion of skin surrounding the skin treatment site. The channel must be designed to receive and guide the plunger therethrough, but does not need to engage the plunger. The channel 30 may be completely encircled by the frame and consist solely of an orifice for receiving the plunger, as shown in FIG. 3. Alternatively, the channel may be defined by at least one portion of the outermost frame edge, and thus include a slit extending from the plunger-receiving portion of the channel to the frame edge, as shown in FIGS. 1, 2, and 8. This slit portion of the channel is useful for receiving a catheter or tube. For example, the slit channel design shown in FIGS. 1, 2, and 8 provides useful means for affixing the frame to a wound having a puncturing device such as an arterial catheter or a drainage tube piercing the wound through the skin, typically extending to an artery or organ.

The frame may be comprised of multiple segments for placement around the skin treatment site, leaving gaps between the frame segments, as long as the design of the frame provides reduced elasticity at the skin treatment site. However, a single-piece frame is preferred.

The frame must be made of a material having a lower elasticity than the skin portion of the wound. Examples of suitable frame materials include polymer films and closed cell type foams such as 3M 1526 Film, 3M 9877 Film, 3M 1773 Foam, and 3M 1776 Foam available commercially from the 3M company. The material used to make the frame is not particularly critical as long as the elasticity is sufficiently low.

The thickness of the frame is preferably greater than the thickness of the strap. A ratio of frame thickness to strap thickness of from about 1:1 to about 50:1 is preferred, with a ratio of about 1:1 to about 25:1 being more preferred.

In the embodiments of the present medical dressing wherein any of the means of affixing is a pressure sensitive adhesive, it is useful to cover the adhesive surface with a release strip such as a silicone coated paper to be removed just prior to the affixing. Such release strips are commonly known and used in the bandage art.

Figure 4:
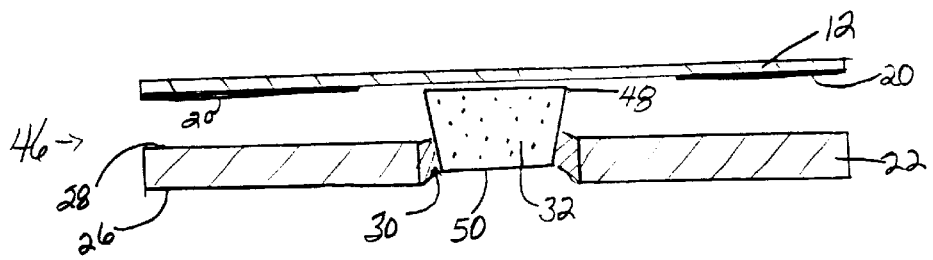
FIG. 4 illustrates a front cross sectional view of the present pressure device wherein the plunger is adhesively bonded to the strap.
Figure 7:
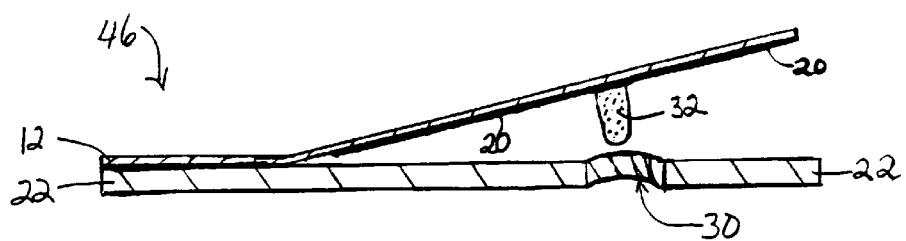
FIG. 7 illustrates a front cross sectional view of the present pressure device wherein the strap and frame are connected at a position distal from the channel prior to use and the plunger is adhesively affixed to the strap.

In addition to the medical dressing, the present invention further includes a medical pressure device 46 for applying pressure to a wound, as shown in FIGS. 2, 3, 4, 5, 7, and 8. The medical device of the present invention is the present dressing, as described above, wherein the strap is adapted to effect a pressure below the lower frame surface, thus into the wound, when the device is affixed to the wound. In the present medical device, the strap is equipped with a plunger 32 having a size sufficient to be slidingly received through the channel 30 of the frame 22. It is critical that the length of the plunger, as defined between an upper plunger end 48 and a lower plunger end 50 is longer than the length of the channel, as measured transversely between the upper frame surface 28 and the lower frame surface 26, so that the plunger is pushed further beyond the lower frame surface when the strap is affixed across the upper frame surface. FIG. 4 shows an embodiment of the device 46 where the plunger 32 is a separate component from the strap 12 and engages with the center area of the strap simply by the strap crossing over the upper plunger end 48 upon attachment of the strap to the frame. FIG. 7 shows an embodiment of the device 46 where the strap and frame are connected at a position distal from the channel 30 and the plunger 32 is engaged with, and adhesively affixed to, the center area of the strap 12.

Figure 5:
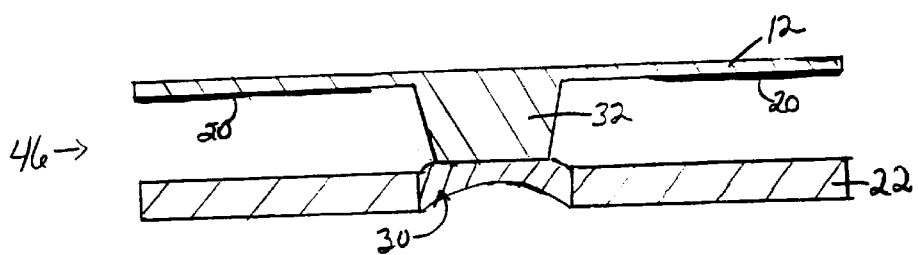
FIG. 5 illustrates a front cross sectional view of the present pressure device wherein the strap and plunger are formed as one integral member.

FIG. 5 illustrates an embodiment of the present pressure device 46 wherein the strap 12 and the plunger 32 are integrally connected together. Such a combination of a strap and plunger is usefully molded from a material such as a rubber or a plastic.

Figure 6:
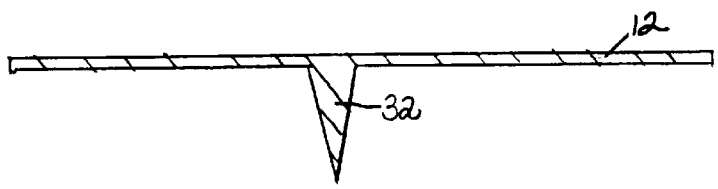
FIG. 6 illustrates a front cross sectional view of the present pressure device wherein the plunger has a sharp lower object end.

The shape of the plunger used in the present pressure device must be suitable for being easily received through the channel 30. The channel is shaped to receive and guide the plunger. No contact or engagement between the channel and the plunger is necessary. It is preferable for the plunger to be elongated between the upper object end and the lower object end. A blunt lower plunger end, as shown in FIGS. 4, 5, and 7 would provide a simulated digital pressure against the wound. A sharp lower plunger end, as shown in FIG. 6, would provide a piercing pressure against the wound.

It is preferred that the plunger used in the present pressure device be constructed from a material harder than the wound. The plunger may be a molded piece, a multi-layered woven pad, an open-cell or closed-cell foam, and such. Examples of materials suitable for forming the plunger include rubber, foam, cellulose, paper such as cardboard, wax, cotton, nylon, plastic, polyurethane, polyester, and polyethylene.

In the present pressure device, the strap should be connected to or affixable to a sufficient amount of surface area of the frame so that the negative pressure exerted by the substrate toward the strap does not displace the strap from the frame. It should be apparent that a greater amount of bonded strap-to-frame surface area would be required to press a plunger further into the wound. For example, a useful medical pressure device designed for applying digital pressure to a puncture site from a typical central line catheter extraction has a plunger of about 0.25 to about 1.0 cm in length, a frame/strap bondable surface of about 25 to about 50 cm$^2$, with a frame thickness of about 0.1 to about 0.5 cm. A preferred ratio of the width across the upper frame surface to the diameter across the channel is about 2:1 to about 10:1, with a ratio of about 3:1 to about 5:1 being more preferred.

The present invention further includes a process of treating a wound. The process of the present invention includes framing the skin treatment site of a wound by affixing a frame having an elasticity less than the elasticity of the skin to the skin annulus. The framing is conducted by affixing the frame to a sufficient amount of the annulus so as to reduce the skin elasticity across the skin treatment site. An elasticity-sensitive procedure is performed on the wound after the framing step is conducted.

The elasticity-sensitive procedure performed on the framed wound is preferably selected from the group of procedures consisting of applying pressure, cutting, piercing, tearing, rubbing, and such. The application of blunt pressure is the more preferred elasticity-sensitive procedure of the present invention. The present process is most preferably conducted as a digital pressure process carried out using the pressure device of the present invention, particularly when using a plunger having a hardness greater than the hardness of the wound. It is preferable that the digital pressure process be conducted sufficiently so that the plunger forcibly indents the wound as it presses against the treatment site.

Of the elasticity-sensitive procedures listed above, the most preferred procedure is the application of blunt pressure in order to promote rapid clotting of blood, hemostasis, subsequent to a medical therapy or test. Examples of suitable types of wounds for which the present process would be useful in effecting hemostasis through the application of blunt pressure includes the wounds resulting from therapies and tests involving arterio punctures made by a syringe for injection or blood withdrawal, punctures made from catheters during hemodialysis, arteriography, and percutaneous transcatheter angioplasty, non-arterial wound drainage tubes, intravenous ports, stab wounds, gun shots. In addition to hemostasis after a medical therapy or test, the present invention is also beneficial in effecting hemostasis of punctures, lacerations, and ragged cuts in emergency or non-emergency settings outside of a clinical setting.

The process of the present invention further includes using the present pressure device equipped with a plunger doped with a composition of matter so that the composition of matter is pressurably contacted with the treatment site. This particular process would be most beneficial for administration of a composition that is more readily absorbed through the skin and into the wound when contacted with the skin under pressure. Examples include hydrophobic drugs and nutrients. The plunger may be formed from a solid composition of matter that is useful itself in effecting a chemical reaction to the wound. Examples of such plunger materials include wax-based drug compositions, and other compositions that are hard solids at room temperature.

Various non-medical applications of the present invention can be appreciated for treating a soft substrate that is covered with an elastic surface. Examples of such substrates include plant tissues, rubber articles, elastic plastic articles (including polyesters, polypropylene, and such), foam articles, woven articles, stuffed and filled articles, and such. Examples of applications include repairing substrates such as swimming pool liners, inner tubes, and upholstered furniture.

In the drawings and specification, there have been disclosed typical preferred embodiments of the invention and, although specific terms are employed, they are used in a generic and descriptive sense only and not for purposes of limitation, the scope of the invention being set forth in the following claims.

I claim:

1. A catheterization pressure bandage comprising:
   (a) a frame having an upper frame surface, a lower frame surface adapted to be positionable against a patient's skin, an outermost frame edge, a channel having a channel length extending transversely between said upper frame surface and said lower frame surface, and a slit connecting said channel with said outermost frame edge thereby providing lateral access to said channel;
   (b) a strap connected to said upper frame surface, said strap comprising an upper strap surface, a lower strap surface having a center area surrounded by an outer area, wherein said outer area of said lower strap surface is adapted to be supportively positioned across said upper frame surface thus providing overlapping surface areas on said frame and said strap, a portion of said overlapping surface areas of said frame and said strap distal to one side of said channel being connected together, a plunger affixed to and extending transversely from said center area to a plunger end defining a plunger length therebetween that is greater than said channel length, and further wherein said plunger has a shape adapted to be receivable through said channel to extend beyond said lower frame surface when said strap is lowered onto said frame;

(c) a layer of releasable adhesive disposed across said lower frame surface for attaching said frame to the patient's skin; and (d) a layer of pressure sensitive adhesive disposed across at least one of said overlapping surface areas of said strap and said frame, wherein said overlapping surface areas are sufficiently large so that, when said lower frame surface is attached to the patient's skin and then said overlapping surface areas are adhered together, said plunger will tend to exert a higher pressure towards the patient than towards the strap.

2. The catheterization pressure bandage according to claim 1 wherein said connected portion of said overlapping surface areas is at least about 15 percent of total said overlapping surface areas.

3. The catheterization pressure bandage according to claim 2 wherein said connected portion of said overlapping surface areas is at least about 25 percent of total said overlapping surface areas.

4. The catheterization pressure bandage according to claim 1 wherein said plunger is adapted to exert a sufficient amount of pressure against the patient to increase hemostasis of a bleeding wound.

5. The catheterization pressure bandage according to claim 1 wherein said plunger is affixed to said center area of said lower strap surface by way of an adhesive, a hook and loop fastener, or a mechanical fastening mechanism.

6. The catheterization pressure bandage according to claim 5 wherein said plunger is affixed to said center area of said lower strap by way of an adhesive.

7. The catheterization pressure bandage according to claim 1 wherein said slit is adapted to laterally receive a catheterization tube.

8. A catheterization pressure bandage assembly comprising:

(a) a frame having an upper frame surface, a lower frame surface adapted to be positionable against a patient's skin, an outermost frame edge, a channel having a channel length extending transversely between said upper frame surface and said lower frame surface, and a slit connecting said channel with said outermost frame edge thereby providing lateral access to said channel;

(b) a strap comprising an upper strap surface, a lower strap surface having a center area surrounded by an outer area, wherein said outer area of said lower strap surface is adapted to be supportively positioned across said upper frame surface thereby providing overlapping surface areas on said frame and said strap, a plunger affixed to and extending transversely from said center area to a plunger end defining a plunger length therebetween that is greater than said channel length, and further wherein said plunger has a shape adapted to be receivable through said channel to extend beyond said lower frame surface when said outer area of said lower strap is positioned across said upper frame surface;

(c) a layer of releasable adhesive disposed across said lower frame surface for attaching said frame to the patient's skin; and (d) a layer of pressure sensitive adhesive disposed across at least one of said overlapping surface areas of said strap and said frame, wherein said overlapping surface areas are sufficiently large so that, when said lower frame surface is attached to the patient's skin and then said overlapping surface areas are adhered together, said plunger will tend to exert a higher pressure towards the patient than towards the strap.

9. The catheterization pressure bandage assembly according to claim 8 wherein said plunger is affixed to said center area of said lower strap surface by way of an adhesive, a hook and loop fastener, or a mechanical fastening mechanism.

10. The catheterization pressure bandage assembly according to claim 9 wherein said plunger is affixed to said center area of said lower strap surface by way of an adhesive.

11. A pressure bandage assembly comprising:

(a) a frame having an upper frame surface, a lower frame surface adapted to be positionable against a patient's skin, a channel having a channel length extending transversely between said upper frame surface and said lower frame surface, wherein said frame completely surrounds said channel;

(b) a strap comprising an upper strap surface, a lower strap surface having a center area surrounded by an outer area, wherein said outer area of said lower strap surface is adapted to be supportively positioned across said upper frame surface thus providing overlapping surface areas on said frame and said strap, a plunger affixed to and extending transversely from said center area to a plunger end defining a plunger length therebetween that is greater than said channel length, and further wherein said plunger has a shape adapted to be receivable through said channel to extend beyond said lower frame surface when said outer area of said lower strap is positioned across said upper frame surface;

(c) a layer of releasable adhesive disposed across said lower frame surface for attaching said frame to the patient's skin; and (d) a layer of pressure sensitive adhesive disposed across at least one of said overlapping surface areas of said strap and said frame, wherein said overlapping surface areas are sufficiently large so that, when said lower frame surface is attached to the patient's skin and then said overlapping surface areas are adhered together, said plunger will tend to exert a higher pressure towards the patient than towards the strap.

12. The pressure bandage assembly according to claim 11 wherein said plunger is affixed to said center area of said lower strap surface by way of an adhesive, a hook and loop fastener, or a mechanical fastening mechanism.

13. The pressure bandage assembly according to claim 12 wherein said plunger is affixed to said center area of said lower strap surface by way of an adhesive.

14. The pressure bandage assembly according to claim 11 wherein both said strap and said frame are part of an integrally formed foldable strip, wherein said strip is used by folding said strap across said frame.

15. A pressure bandage comprising:
(a) a frame having an upper frame surface, a lower frame surface adapted to be positionable against a patient's skin, a channel having a channel length extending transversely between said upper frame surface and said lower frame surface, wherein said frame completely surrounds said channel;
(b) a strap connected to said upper frame surface, said strap comprising an upper strap surface, a lower strap surface having a center area surrounded by an outer area, wherein said outer area of said lower strap surface is adapted to be supportively positioned across said upper frame surface thereby providing overlapping surface areas on said frame and said strap, a plunger affixed to and extending transversely from said center area to a plunger end defining a plunger length therebetween that is greater than said channel length, a portion of said overlapping surface areas of said frame and said strap distal to one side of said channel being connected together to allow said strap to be lifted away from said channel, and further wherein said plunger has a shape adapted to be receivable through said channel to extend beyond said lower frame surface when said strap is lowered onto said frame;
(c) a layer of releasable adhesive disposed across said lower frame surface for attaching said frame to the patient's skin; and
(d) a layer of pressure sensitive adhesive disposed across at least one of said overlapping surface areas of said strap and said frame,
wherein said overlapping surface areas are sufficiently large so that, when said lower frame surface is attached to the patient's skin and then said overlapping surface areas are adhered together, said plunger will tend to exert a higher pressure towards the patient than towards the strap.

16. The pressure bandage according to claim 15 wherein said connected portion of said overlapping surface areas is at least about 15 percent of total said overlapping surface areas.

17. The pressure bandage according to claim 16 wherein said connected portion of said overlapping surface areas is at least about 25 percent of total said overlapping surface areas.

18. The pressure bandage according to claim 15 wherein said plunger is affixed to said center area of said lower strap surface by way of an adhesive, a hook and loop fastener, or a mechanical fastening mechanism.

19. A process of applying pressure against a wound covered by a skin treatment site, comprising the steps of:
(a) reducing the elasticity of the skin treatment site by adhering a frame substantially around the skin treatment site, said frame having a thickness;
(b) providing a plunger having a first end, an oppositely positioned second end affixed to a center area of a member, and a plunger length between the first and second ends greater than the thickness of said frame;
(c) then placing the first end of said plunger against the skin treatment site; and
(d) thereafter pressing said plunger against the skin treatment site by affixing said member tautly across said frame.

20. The process according to claim 19 wherein said pressing is sufficient to increase the hemostasis of a bleeding wound.

* * * * *